(12) United States Patent
Haupt et al.

(10) Patent No.: US 10,298,816 B2
(45) Date of Patent: May 21, 2019

(54) METHOD OF ASSEMBLING A SUPPLEMENTAL DEVICE COMPRISING A CAMERA MODULE FOR AN INJECTION PEN AND SAID SUPPLEMENTAL DEVICE

(71) Applicant: SANOFI-AVENTIS DEUTSCHLAND GMBH, Frankfurt am Main (DE)

(72) Inventors: Martin Haupt, Vienna (AT); Roman Jiricka, Vienna (AT)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 595 days.

(21) Appl. No.: 14/783,172

(22) PCT Filed: Apr. 16, 2014

(86) PCT No.: PCT/EP2014/057787
§ 371 (c)(1),
(2) Date: Oct. 8, 2015

(87) PCT Pub. No.: WO2014/173774
PCT Pub. Date: Oct. 30, 2014

(65) Prior Publication Data
US 2016/0065799 A1  Mar. 3, 2016

(30) Foreign Application Priority Data

Apr. 22, 2013 (EP) .................................... 13164757

(51) Int. Cl.
*H04N 5/225* (2006.01)
*A61M 5/24* (2006.01)
(Continued)

(52) U.S. Cl.
CPC ............ *H04N 5/2252* (2013.01); *A61M 5/24* (2013.01); *G06K 9/46* (2013.01); *G06K 9/6215* (2013.01);
(Continued)

(58) Field of Classification Search
CPC ................................................... H04N 5/2252
See application file for complete search history.

(56) References Cited

U.S. PATENT DOCUMENTS

| 2003/0032868 A1 | 2/2003 | Graskov et al. |
| 2011/0295215 A1 | 12/2011 | Nielsen et al. |

(Continued)

FOREIGN PATENT DOCUMENTS

| CN | 1525832 | 9/2004 |
| CN | 102905613 | 1/2013 |

(Continued)

OTHER PUBLICATIONS

European Search Report for EP Application No. 13164757, completed Sep. 26, 2013.
International Search Report and Written Opinion for Int. App. No. PCT/EP2014/057787, dated Jun. 2, 2014.

*Primary Examiner* — James M Pontius
(74) *Attorney, Agent, or Firm* — Fish & Richardson P.C.

(57) ABSTRACT

A method of assembling an apparatus for use in performing pattern recognition, the method involves placing a module and a housing relative to one another, the housing being supported relative to an object having an optical marker, and the module comprising a camera for generating a camera output indicative of a scene in the field-of-view of the camera, using the camera output to determine the position of the marker in the field-of-view of the camera, moving the module and the housing relative to one another until the marker is at a predetermined location in the field-of-view of the camera and then fixing the position of the module relative to the housing.

14 Claims, 8 Drawing Sheets

(51) Int. Cl.
*G06K 9/46* (2006.01)
*G06K 9/62* (2006.01)
*G06T 7/00* (2017.01)
*G06T 7/70* (2017.01)
*A61M 5/31* (2006.01)

(52) U.S. Cl.
CPC .............. G06T 7/0014 (2013.01); G06T 7/70 (2017.01); H04N 5/2256 (2013.01); H04N 5/2257 (2013.01); *A61M 2005/3125* (2013.01); *A61M 2005/3126* (2013.01); *A61M 2205/3592* (2013.01); *A61M 2205/502* (2013.01)

(56) References Cited

U.S. PATENT DOCUMENTS

| | | |
|---|---|---|
| 2012/0053527 A1 | 3/2012 | Cirillo et al. |
| 2013/0197445 A1 | 8/2013 | Schabbach et al. |
| 2018/0038501 A1* | 2/2018 | Peret .................... A61M 5/1411 |

FOREIGN PATENT DOCUMENTS

| | | |
|---|---|---|
| EP | 1475960 | 11/2004 |
| JP | 2004/334794 | 11/2004 |
| JP | 2010/130545 | 6/2010 |
| JP | 2012/504440 | 2/2012 |
| WO | 2010/037828 | 4/2010 |
| WO | 2011/117212 | 9/2011 |
| WO | WO 2013/004843 | 1/2013 |

* cited by examiner

METHOD OF ASSEMBLING A SUPPLEMENTAL DEVICE COMPRISING A CAMERA MODULE FOR AN INJECTION PEN AND SAID SUPPLEMENTAL DEVICE

CROSS REFERENCE TO RELATED APPLICATIONS

The present application is a U.S. National Phase Application pursuant to 35 U.S.C. § 371 of International Application No. PCT/EP2014/057787 filed Apr. 16, 2014, which claims priority to European Patent Application No. 13164757.0 filed Apr. 22, 2013. The entire disclosure contents of these applications are herewith incorporated by reference into the present application.

TECHNICAL FIELD

An aspect of the present invention relates to a method of assembling an apparatus for use in performing pattern recognition (such as optical character recognition). Another aspect of the present invention relates to a pattern recognition apparatus.

BACKGROUND

A variety of diseases exist which require regular treatment by injection of a medicament. Such injection can be performed by either medical personnel or by patients themselves. As an example, type-1 and type-2 diabetes can be treated by patients themselves by injection of insulin doses once or several times per day. It is known to couple a supplemental device to an insulin injection device for recording information about the doses that are administered. Supplemental devices may be used to record information about the various times at which insulin doses are administered and the quantity of insulin administered during each such dose.

One previously proposed insulin injection device, specifically the Solostar™ injection pen sold by Sanofi, is provided with a window in its outer surface (hereafter referred to as a dosage window). A sleeve inside the Solostar™ injection pen (known as the number sleeve) is caused to rotate when an amount of insulin is dialled or dispensed. Numbers on the number sleeve successively align with the dosage window as the sleeve rotates. When an amount of insulin has been dialled, the number corresponding to the dialled amount of insulin (in International Units) is displayed in the dosage window. When insulin is dispensed, rotation of the number sleeve causes the number displayed in the dosage window to be that associated with the dialled amount of insulin remaining in the pen yet to be dispensed.

WO2011/117212 describes a supplemental device, provided with optical character recognition (OCR) functionality, for reading numbers aligned with the dosage window of an injection device to determine quantities of insulin dialled or delivered. Supplemental devices which use OCR for this purpose obstruct the view of numbers aligned with the dosage window in use. A display unit may therefore be provided for displaying an indication to a user of the determined amount of insulin dialled or, in the case of an injection, for displaying an indication of the progress of the injection.

It will be appreciated that indications on such a display unit are required to correspond with the actual quantity of insulin dialled or dispensed. In other words, the indications shown by the display unit should be updated as quickly as possible after a quantity of insulin has been dialled or dispensed. In the case of the Solostar™ injection pen for instance, an amount of insulin is selected by a user turning a dose dialling knob in a series of twists. After each such twist, the indication shown by the display unit of the currently selected insulin amount should be updated as quickly as possible to reduce the likelihood of a user unnecessarily dialling additional dose. Optimally, the optical character recognition algorithm used to determine the particular numbers aligned with the dosage window should be as efficient as possible.

Aspects of the present invention have been conceived with the foregoing in mind.

SUMMARY

According to an aspect of the present invention there is provided a method of assembling an apparatus for use in performing pattern recognition, the method comprising:
  placing a module and a housing relative to one another, the housing being supported relative to an object having an optical marker, and the module comprising a camera for generating a camera output indicative of a scene in the field-of-view of the camera;
  using the camera output to determine the position of the marker in the field-of-view of the camera;
  moving the module and the housing relative to one another until the marker is at a predetermined location in the field-of-view of the camera and then fixing the position of the module relative to the housing.

Advantageously, this reduces adverse effects caused by camera misalignment when using an apparatus to perform pattern recognition.

Moving the module and the housing relative to one another may comprise translating the module and the housing relative to one another.

Moving the module and the housing relative to one another may comprise translating the module and the housing relative to one another without rotation of the module and the housing relative to one another.

Placing the module and the housing relative to one another may comprise placing the module and the housing against one another.

Fixing the position of the module relative to the housing may comprise fixing the module to the housing.

The method may further comprise the step of illuminating the optical marker.

An illumination device provided on the module may be used to illuminate the optical marker.

The module and the housing may comprise first and second support portions respectively that are configured to support the module and the housing relative to one another when brought into engagement; and the step of placing the module and the housing relative to one another may comprise engaging the first and second support portions.

Moving the module and the housing relative to one another may comprise moving one of the support portions within a channel defined by the other support portion.

Advantageously this guides the movement of the module and the housing relative to one another.

The step of determining the position of the marker in the field-of-view of the camera may comprise: comparing the camera output with a template, the template being indicative of where the marker is intended to be located in the field-of-view of the camera; determining the difference between the position of the marker in the field-of-view of the camera and the intended position of the marker in the field-of-view of the camera; and determining the extent to which the camera and the marker should be moved relative to one another to offset the difference in positions.

The method may further comprise continually monitoring the difference in positions until such difference has been offset.

The apparatus may be a supplemental device for determining an amount of dose delivered by an injection device, and the object may correspond in shape to the part of an injection device to which the supplemental device is configured to be coupled in use.

Advantageously, assembling a supplemental device according the foregoing method reduces adverse effects caused by camera misalignment when determining an amount of dose delivered by an injection device.

According to another aspect of the present invention there is provided a pattern recognition apparatus, the apparatus comprising:
- a module comprising a camera for generating a camera output indicative of a scene in the field-of-view of the camera; and
- a housing fixed to the module in a rigid manner by a fixing;
- wherein the module and the housing comprise first and second support portions respectively, one of the support portions defining a channel in which the other of the support portions would be able to translate in a confined manner in the absence of the fixing.

In the absence of the fixing the support portion may be able to translate along an axis relative to one another without rotation of the support portions relative to one another.

The apparatus may be a supplemental device for determining an amount of dose delivered by an injection device, and the apparatus may be configured to be coupled to an injection device in use.

According to a further aspect of the present invention there is provided a system for assembling an apparatus for use in performing pattern recognition, the system comprising:
- a placer for placing a module and a housing relative to one another, the housing being supported relative to an object having an optical marker, and the module comprising a camera for generating a camera output indicative of a scene in the field-of-view of the camera;
- a determiner for using the camera output to determine the position of the marker in the field-of-view of the camera;
- a mover for moving the module and the housing relative to one another until the marker is at a predetermined location in the field-of-view of the camera; and
- a fixer for fixing the position of the module relative to the housing when the marker is at the predetermined location in the field-of-view of the camera.

According to another aspect of the present invention there is provided a pattern recognition apparatus, the apparatus comprising:
- a module comprising a camera for generating a camera output indicative of a scene in the field-of-view of the camera; and
- a housing configured to be fixed to the module in a rigid manner by a fixing;
- wherein the module and the housing comprise first and second support portions respectively, one of the support portions defining a channel in which the other of the support portions would be able to translate in a confined manner;
- wherein the camera output is used to determine a position of a marker in the field-of-view of the camera;
- and wherein the module and the housing are fixed to each other in a position wherein the marker is at a predetermined position in the field-of-view of the camera.

DETAILED DESCRIPTION

In the following, embodiments of the present invention will be described in the context of a supplemental device for determining an amount of dose dialled, or an amount of dose dispensed, by an injection device. Such a supplemental device may be provided with optical character recognition (OCR) functionality for making such a determination. The present invention is however not limited to such application and may equally well be deployed with other devices that are capable of implementing OCR functionality.

Figure 1:
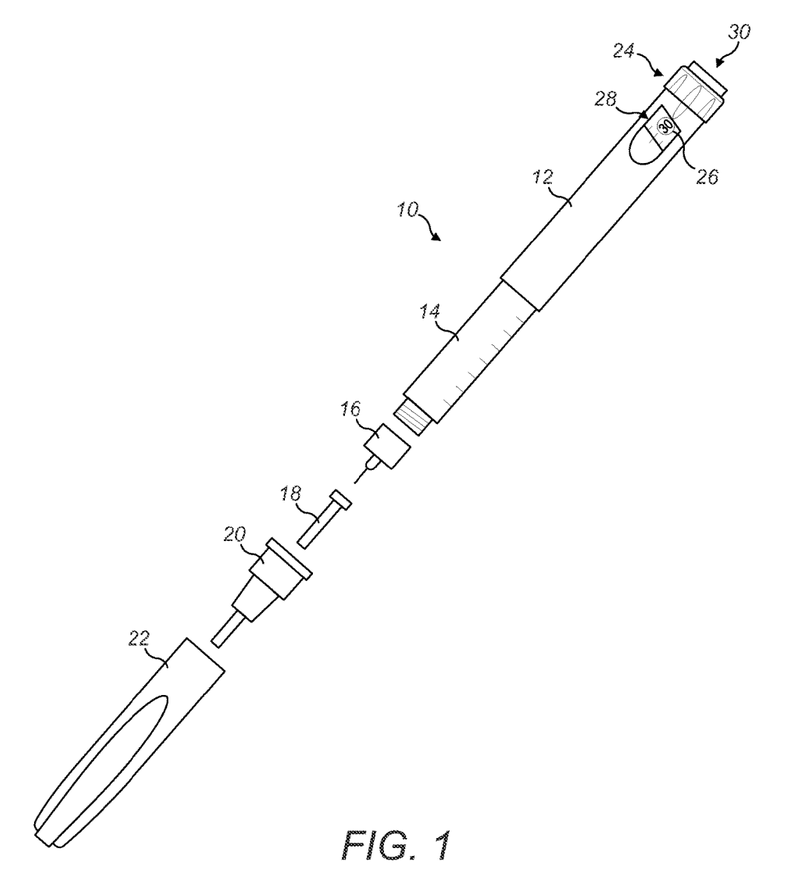
FIG. 1 is a schematic view of an exemplary injection device.

FIG. 1 is an exploded view of an injection device 10, which may for instance represent the Solostar™ injection pen sold by Sanofi.

The injection device 10 of FIG. 1 is a pre-filled, disposable injection pen that comprises a housing 12 and contains an insulin container 14, to which a needle 16 can be affixed. The needle 16 is protected by an inner needle cap 18 and an outer needle cap 20, which in turn can be covered by a cap 22. An insulin dose to be ejected from injection device 10 can be selected by turning the dosage knob 24 (this act may be referred to as dialling an insulin dose). Markers representing numbers 26 indicative of the selected dose (the dialled dose) are displayed via dosage window 28 in multiples of International Units (IU) for instance. An example of a dialled dose displayed in the dosage window 28 may be 30 IUs, as shown in FIG. 1.

The numbers 26 displayed in the dosage window 28 are printed on a sleeve (known as the number sleeve 17) contained in the housing 12 and which mechanically interacts with a piston inside the insulin container 14. When needle 16 is stuck into the skin of a patient and the injection button 30 is pushed, an amount of insulin corresponding to the dialled quantity displayed in the display window 28 is ejected from the injection device 10. During the course of the injection, as insulin leaves the injection device 10 the number sleeve 17 rotates. This causes the number 26 displayed in the dosage window 28 to change in accordance with the dialled amount of insulin yet to be dispensed. In other words, during the course of an injection the numbers 26 that successively align with the dosage window 28 are caused to count down.

Figure 2:
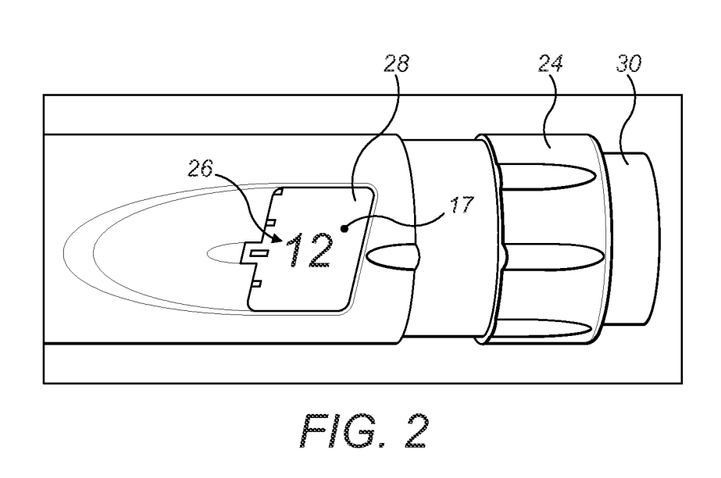
FIG. 2 is an enlarged view of an end of the injection device in FIG. 1.

FIG. 2 shows the dosage window 28 after some of the 30 IUs of insulin previously dialled have been delivered from the injection device 10 during the course of the injection in the preceding paragraph.

Figure 3:
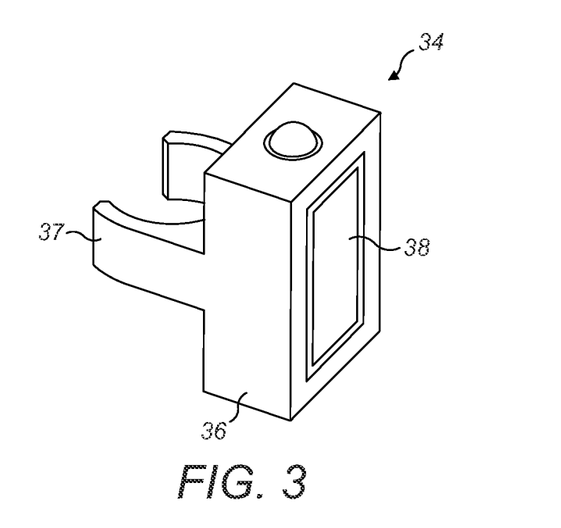
FIG. 3 is a schematic view of a supplemental device according to one embodiment of the present invention.

FIG. 3 is a schematic illustration of a supplemental device 34 which may be releasably attached to an injection device such as the one depicted in FIG. 1. The supplemental device 34 comprises a housing 36 that may comprise multiple parts. The housing 36 is provided with a mating unit 37 for embracing the housing 12 of an injection device 10. In particular the mating unit 37 may be configured to snap-fit onto the housing 12 of an injection device 10 in such a way that the device 34 can be subsequently removed therefrom. The mating unit 37 need not however be of the snap-fit variety and other arrangements may alternatively be suitable for coupling the supplemental device 34 to an injection device 10.

Figure 4:
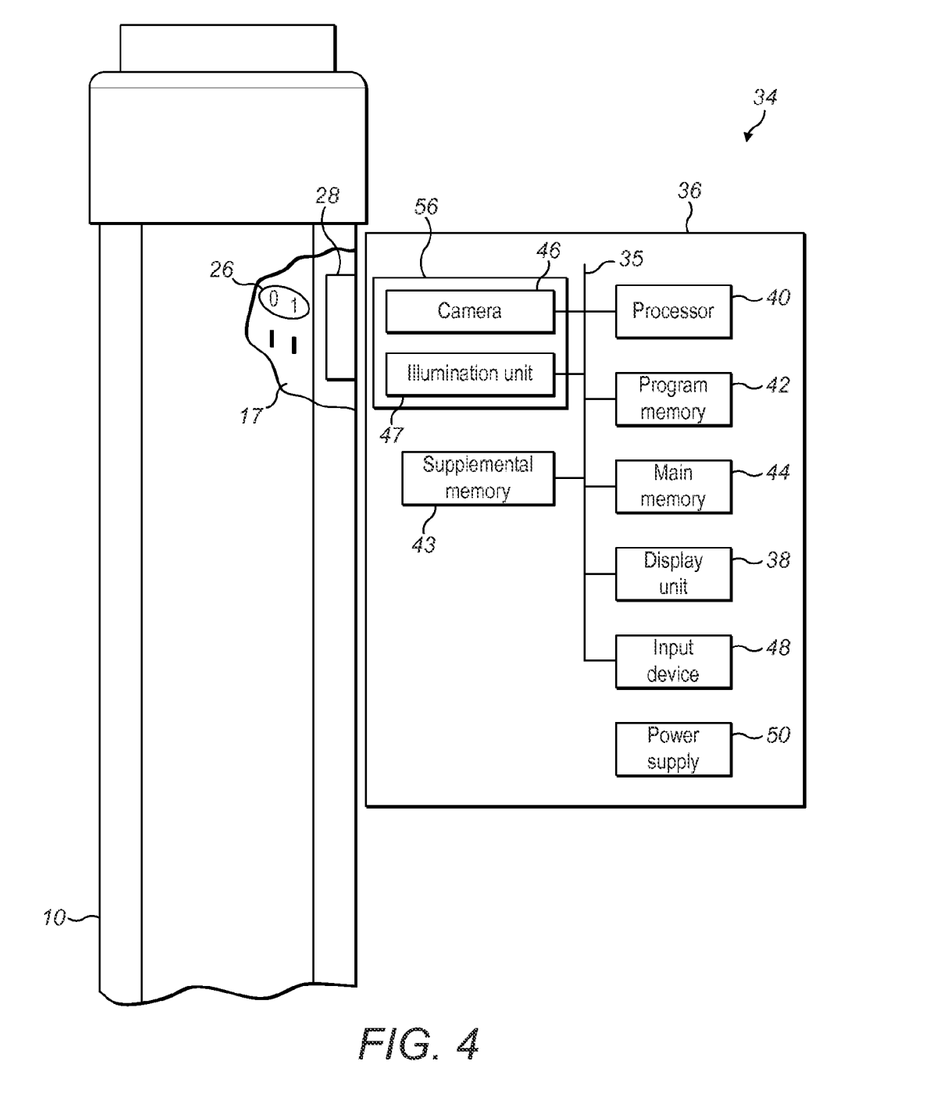
FIG. 4 is a schematic internal view of the supplemental device in FIG. 3.

When coupled to an injection device 10, the supplemental device 34 obstructs the dosage window 28 (as in FIG. 4). The supplemental device 34 comprises a camera for gathering information from the injection device 10. In particular the camera (described in more detail later on) is used to gather information indicative of what is displayed in the dosage window 28. This gathered information is capable of being processed for generating a dose history database. Such a dose history database may include records containing information about the various times at which insulin doses are administered and the quantity of insulin administered during each dose. The gathered information may also be processed for the purpose of displaying the particular number 26 currently aligned with the dosage window 28 in larger format. This may be achieved, for example, by displaying the number 26 aligned with the dosage window 28 on a display unit in larger form than it appears on the number sleeve 17. This will improve the readability of the amount of dose dialled or, in the case of an injection, the dialled dose amount yet to be delivered.

FIG. 4 illustrates an internal schematic view of the supplemental device 34 in a state where it is coupled to an injection device 10.

Within the housing 36 of the supplemental device 34, a variety of components are located and coupled together by a system bus 35. One such component includes a processor 40. Program memory 42 and main memory 44 are also coupled to the system bus 35. The processor 40 executes program code (e.g. software or firmware) stored in the program memory 42 and uses the main memory 44 to store intermediate results. The supplemental device 34 also comprises a supplemental memory 43 for storing the aforementioned dose history database. Program memory 42 may for instance be non-volatile memory such as Read-Only Memory. Main memory 44 may for instance be a volatile memory such as Random Access Memory, DRAM or SDRAM. Supplemental memory 43 may for instance be Flash memory or an EEPROM or may comprise a memory card coupled to the system bus 35 via an interface such as a USB-type connection.

A camera 46, also coupled to the system bus 35, is used to generate signals containing information indicative of what is displayed in the dosage window 28. The processor 40 may use these signals to generate the dose history database. The processor 40 could do this by executing an OCR application to determine, from signals sent by the camera 46, which number is aligned with the dosage window 28. On the basis of such information the processor 40 then determines how much insulin has been dialled or, in the case of an injection, the dialled amount of insulin that remains to be delivered (or has already been delivered during the course of the injection). In some embodiments however the camera 46 may itself be capable of implementing the OCR functionality such that the signals it outputs to the processor 40 are indicative of the number aligned with the dosage window 28. The processor 40 may then on the basis of this information determine as above how much insulin has been dialled or, in the case of an injection, the dialled amount of insulin that remains to be delivered (or has already been delivered during the course of the injection).

Other components which may be coupled to the system bus 35 include an illumination unit 47, a display unit 38 and an input device 48. Such an illumination unit 47 may include one or more LEDs and may be controlled by the processor 40 to illuminate information displayed in the dosage window 28. An input device 48 (for example, a keypad) may be utilised by a user to interact with the supplemental device 34. Such an input device 48 may for instance be used to select one or more options shown on a display unit 38. In some embodiments a display unit 38 may be provided with touch-screen functionality thus enabling it to function as both an output device and the input device 48.

A power supply source 50 (for example a battery) is for powering the various components of the supplemental device 34.

Details of the camera 46 will now be outlined in further detail. Specifically, how the camera 46 is included in the supplemental device 34 during assembly will now be outlined with reference to FIG. 5.

Figure 5:
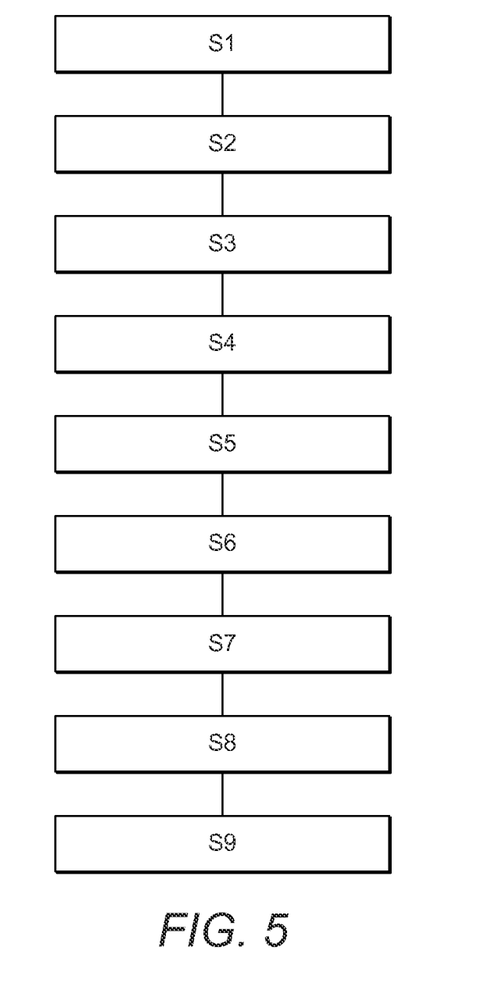
FIG. 5 is a flow diagram of a process according to an embodiment of the present invention.
Figure 6:
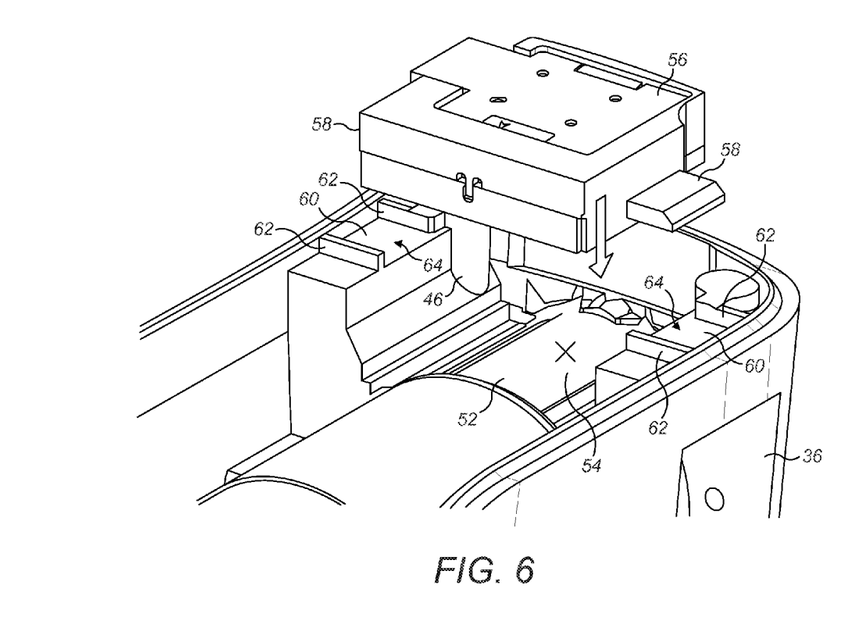
FIG. 6 is a schematic view of a module prior to being placed on a housing.

During assembly of the supplemental device 34, in step S1 the housing 36 (or a part thereof in the instance that the housing 36 comprises multiple parts) is supported relative to a reference object 52. This is illustrated in FIG. 6. The reference object 52 corresponds in shape to the part of an injection device 10 to which the supplemental device 34 (once assembled) is configured to be coupled in use and may for instance comprise a reference pin. Persons skilled in the art will understand that the reference object 52 may comprise a single-piece object produced using a single-stage injection moulding process for example. Regardless of how the reference object 52 is made, a marker 54 (such as a cross, dot or other indicator) is located on the reference object 52 in a corresponding location that a number 26 would otherwise be viewable when aligned with the dosage window 28 were the reference object 52 in fact an injection device 10. In other words, a marker 54 may be located on the reference object 52 in a corresponding location to the number "12" shown in FIG. 2.

The step of supporting the housing 36 relative to a reference object 52 in step S1 could involve coupling the housing 36 to the reference object 52 using mating unit 37 (see FIG. 3) already coupled to the housing 36 or comprising an integral part thereof. Alternatively step S1 could involve a device, such as a robotic arm, holding the housing 36 relative to the reference object 52 in the position that the housing 36 would otherwise be located relative to the reference object 52 if they were coupled to one another in the manner described in the foregoing sentence.

In step S2, a module 56 comprising the camera 46 is placed relative to the housing 36. This may involve a device, such as a robotic arm, placing the module 56 relative to the housing 36. Furthermore, placing the module 56 relative to the housing 36 could involve placing the module 56 and the housing 36 against one another as in FIG. 7. The module 56 and the housing 36 may for instance comprise first and second support portions respectively. These support portions define separate parts of a two-part engagement mechanism which, when engaged, support the module 56 and housing 36 relative to one another. In the example shown in FIG. 6, the module 56 and the housing 36 together comprise a pair of two-part engagement mechanisms. The first part of each such engagement mechanism comprises a protrusion 58 defining a planar surface, one of which extends from either side of the module 56. The second part of each such engagement mechanism comprises a guide 60 defining a planar surface, one of which extends internally from either side of the housing 36.

Figure 7:
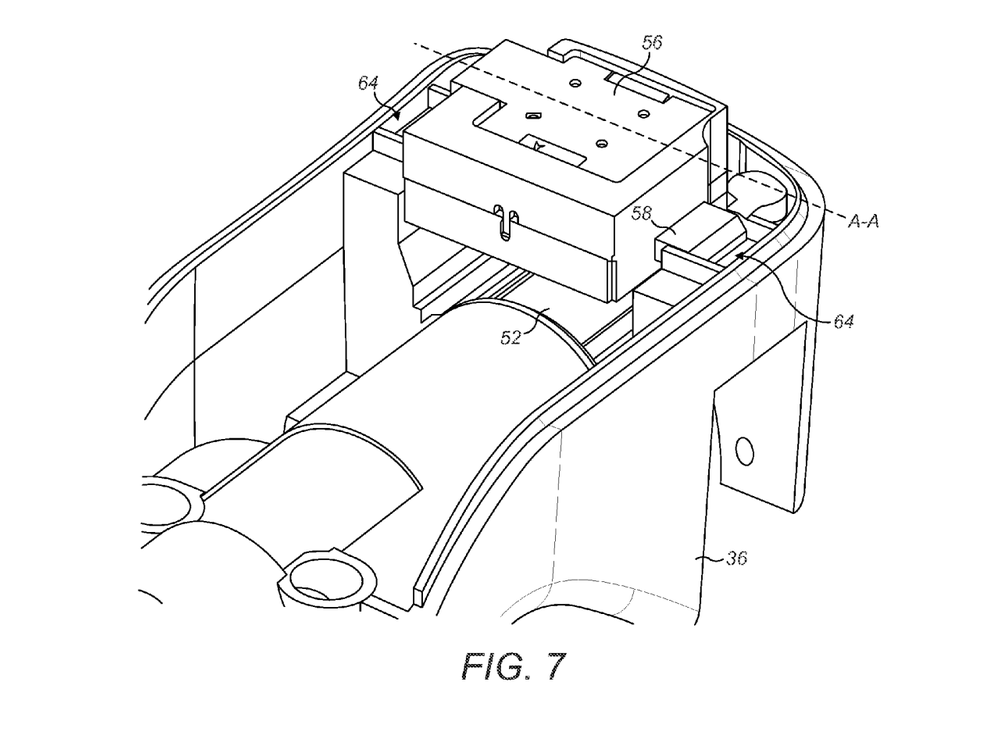
FIG. 7 is a schematic view of a module after being placed on a housing.

Upon comparing FIGS. 6 and 7 it will be appreciated that in the present example, placing the module 56 relative to the housing 36 involves engaging the planar surfaces defined by the respective protrusions 58 and guides 60. It will also be appreciated that the protrusions 58 may instead extend internally from either side of the housing 36 and the module may define guides 60.

Figure 8:
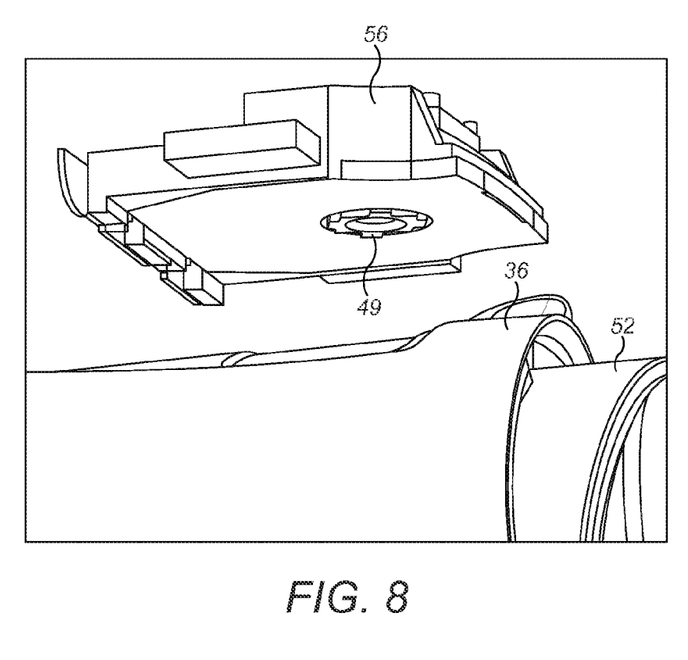
FIG. 8 is a schematic underside view of the module in FIG. 6.

In step S3, the camera 46 is used to generate camera output indicative of a scene in the field-of-view of the camera 46. This may involve connecting a peripheral processing device (not shown) such as an external computer to the camera 46 for controlling the camera 46 to generate camera output. The camera 46 of the module 56 is directed towards the reference object 52 as shown in FIG. 8. Here the camera 46 is aligned with an aperture 49 through which it is able to view the marker 54. Thus by analysing the camera output the peripheral processing device is able to determine the location of the marker 54 within the field-of-view of the camera 46 in step S4.

The peripheral processing device then in step S5 compares the determined location of the marker 54 in the filed-of-view of the camera 46 with a template stored in a memory for example. This template is indicative of the intended location of the marker 54 in the field-of-view of the camera 46. Step S5 is represented diagrammatically in FIG. 9, wherein the intended location of the marker 54 in the field-of-view of the camera 46 is represented by the location at which the cross-hairs 65 intersect.

Next, in step S6 the peripheral processing device determines the difference between the actual position of the marker 54 in the field-of-view of the camera 46 and the intended position of the marker 54 in the field-of-view of the camera 46. This information is used in step S7 to determine the extent to which the camera 46 and the marker 54 should be moved relative to one another to offset the difference between the actual and intended positions mentioned in the previous sentence. This is equivalent to the extent to which the module 56 and the housing 36 should be moved relative to one another since the relative position of the housing 36 and the reference object 52 is fixed.

Figure 10:
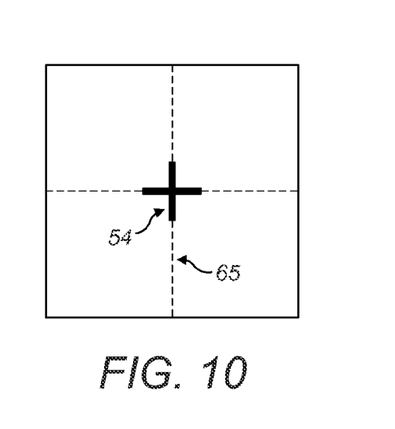
FIG. 10 is a diagrammatic representation of a marker in the field-of-view of a camera after camera alignment.

In step S8 the module 56 and the housing 36 are moved relative to one another until the marker 54 is located at the intended position in the field-of-view of the camera 46 as shown diagrammatically in FIG. 10. This may involve causing either of the aforementioned robotic arms to move the module 56 and housing 36 relative to one another the extent determined in step S7.

In some embodiments step S8 may further involve the peripheral processing device continually monitoring the position of the marker 54 in the field-of-view of the camera 46 while the module 56 and housing 36 are moved relative to one another. This may be carried out to monitor the difference between the actual and the intended position of the marker 54 in the field-of-view of the camera 46 on-the-fly for the purpose of controlling the relative movement of the module 56 and housing 36 in real-time. Alternatively, in other embodiments rather than continually monitoring the position of the marker 54 in the field-of-view of the camera 46, the peripheral processing device may check whether the marker 54 is in the intended position in the field-of-view of the camera 46 after the module 56 and housing 36 have been moved relative to one another. If a negative determination is made then steps S3 to S8 are repeated until the marker 54 is located in the intended position in the field-of-view of the camera 46.

In view of the foregoing, step S8 in the example shown in FIGS. 6 and 7 involves sliding the protrusions 58 across the guides 60. The range of movement of the protrusions 58 is restricted in this particular example by walls 62 which thereby define channels 64. Looking at FIG. 7 the channels 64 provide that, in the present example, the module 56 may only slide along the axis A-A relative to the marker 54. In other embodiments the space between walls 62 may be such that the channels 64 are wider than the protrusions 58. This will allow the module 56 to be additionally slid relative to the marker 54 along an axis perpendicular to the one denoted A-A. Furthermore, such walls 62 may alternatively not be provided.

In step S9, the position of the module 56 relative to the housing 36 is fixed. In the present example this may involve one or more of clamping, adhering or welding the module 56 to the housing 36. This provides that the module 56 and housing 36 are fixed relative to one another in a position where the marker 54 is located in the intended position in the field-of-view of the camera 46. Therefore, in use, numbers 26 on the number sleeve 17 of an injection device 10 will move through this position in the field-of-view of the camera 46.

Other components of the supplemental device 34 may subsequently be coupled to the housing 36 in ways familiar to persons skilled in the art (unless they were coupled to the housing 36 before the module 56). Also the housing 36, if it comprises multiple parts, may be sealed shut by coupling the various parts of the housing 36 together.

Advantageously, assembling a supplemental device 34 according the process described herein reduces adverse effects caused by camera misalignment with numbers 26 in the dosage window 28 of an injection device 10. In particular, the effects of such misalignment are reduced without enhancing the algorithm used to perform OCR.

The scope of the present invention is not restricted to the embodiments illustrated in FIGS. 6 to 8. In some embodiments, the module 56 may not be coupled directly to the housing. For example, a component such as a battery module (not shown) may be fixed to the housing 36, and the module 56 may be fixed to the battery module in a similar manner to that heretofore described. In particular, the module 56 and the battery module may comprise first and second parts of a two-part engagement mechanism respectively. For example the module may comprise a protrusion 58 and the battery module may define a guide 60 to which the protrusion may be coupled. It will be appreciated that since the battery module, for instance, is fixed to the housing 36, moving the module 56 relative to the battery module during assembly will have the same effect as moving the module 56 relative to the housing 36. In this way the camera 46 can be moved relative to the marker 54 until the marker 54 is located in the intended position in the field-of-view of the camera 46. The module 56 is then fixed to the battery module, for instance, with the camera 46 in this position.

Figure 11:
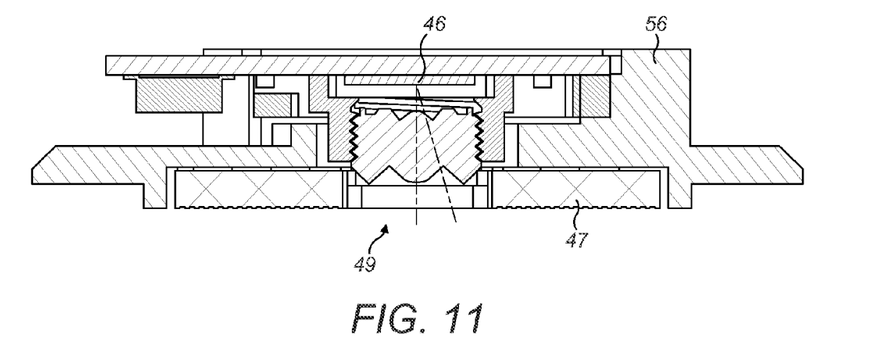
FIG. 11 is a schematic cross-sectional view of a module according to another embodiment of the present invention.

Also, the module 56 may further comprise the illumination unit 47. A cross-section through a module 56 comprising such an illumination unit 47 is illustrated in FIG. 11. Therefore, step S3 may further involve the peripheral processing device (not shown) controlling the illumination unit 47 to illuminate the marker 54 provided on the reference object 52.

The marker 54 may be provided on a transparent area of the reference object 52 which is capable of being backlit. An illumination unit may be located behind the marker 54. Step S3 may thus further involve activating such an illumination unit for the purpose of directing light towards the camera 46 via the transparent area of the reference object 52 on which the marker 54 is provided. This improves the visibility of the marker 54.

It is also envisaged that step S8 could involve rotating the module 56 relative to the housing 36. To enable this, the module 56 may be able to pivot about the respective protrusions 58 for instance. In such an embodiment, step S9 will therefore involve fixing the rotational position of the module 56.

Figure 12:
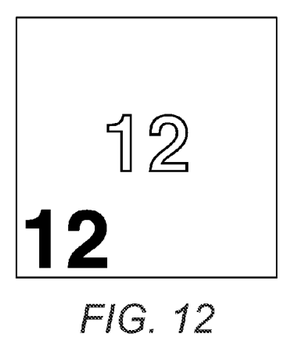
FIG. 12 is a diagrammatic representation of a number in the field-of-view of a camera prior to camera alignment.
Figure 13:
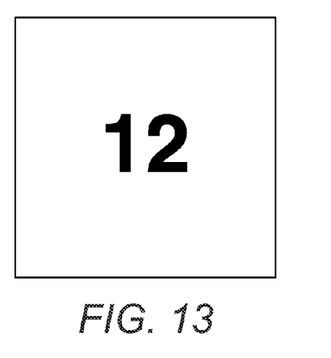
FIG. 13 is a diagrammatic representation of a number in the field-of-view of a camera after camera alignment.

It is also envisaged that instead of using a reference object 52 to align the camera 46 in the manner described herein, an injection device 10 may instead be used for the same purpose. In this way, instead of using a marker 54 to align the camera 46 a number, for instance "0" or "12" on the number sleeve 17, may be used for the same purpose as shown diagrammatically in FIGS. 12 and 13.

Although embodiments of the present invention have been described in the context of a supplemental device 34 for implementing OCR functionality, it will be appreciated that the scope of the present invention is not limited in this regard. More specifically OCR is only one type of pattern recognition functionality. The teachings of the present invention may be applied in the context of a device, for instance a supplemental device 34, for implementing any type of pattern recognition functionality. In such cases, instead of numbers 26 the supplemental device 34 for instance could be used to recognise letters, symbols or respective sections of a code provided on the number sleeve 17 of an injection device 10. Upon determining which letter(s), symbol(s) or code section(s) is(are) displayed in the dosage window 28 of such an injection device 10, the processor 40 may determine an amount of dose dialled or, during the course of an injection, the dialled amount of dose yet to be delivered (or has already been delivered during the course of the injection).

Figure 9:
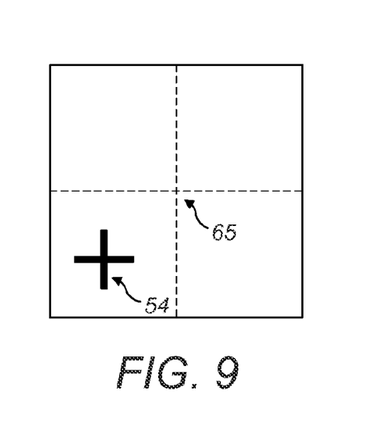
FIG. 9 is a diagrammatic representation of a marker in the field-of-view of a camera prior to camera alignment.

It will be appreciated that an operator may implement one or more of the steps in FIG. 5. For instance, the camera output generated in step S3 may be shown on an operator's monitor. The operator may thus view what is shown in FIG. 9 for example. The operator then moves the module 56 and housing 36 relative to one another until the marker 54 displayed on their monitor is located at the intersection of the crosshairs 65. In this example once this has occurred the operator's monitor will display what is shown in FIG. 10. The operator may physically manipulate the module 56 in order to move it relative to the housing 36 or alternatively they may use a manually operated device for this purpose such as a clamping tool comprising a micrometer screw.

Lastly, it will be appreciated that the above described embodiments are purely illustrative and are not limiting on the scope of the invention. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A method of assembling a supplemental device for determining an amount of dose delivered by an injection device, the supplemental device comprising a module and a housing, and the method comprising:
    placing the module and the housing relative to one another, the housing being supported relative to an object which has an optical marker provided thereon, the object corresponding in a shape to a part of the injection device to which the supplemental device is configured to be coupled in use, and the module comprising a camera for generating a camera output indicative of a scene in a field-of-view of the camera;
    using the camera output to determine a position of the optical marker in the field-of-view of the camera;
    comparing the position of the optical marker with a template indicative of a predetermined location of the optical marker in the field-of-view of the camera;
    moving, based on the comparing, the module and the housing relative to one another until the optical marker is at the predetermined location in the field-of-view of the camera; and
    once the optical marker is at the predetermined location, fixing a position of the module relative to the housing.

2. The method of claim 1, wherein moving the module and the housing relative to one another comprises translating the module and the housing relative to one another.

3. The method of claim 1, wherein moving the module and the housing relative to one another comprises translating the module and the housing relative to one another without rotation of the module and the housing relative to one another.

4. The method of claim 1, wherein placing the module and the housing relative to one another comprises placing the module and the housing against one another.

5. The method of claim 1, wherein fixing the position of the module relative to the housing comprises fixing the module to the housing.

6. The method of claim 1, further comprising the step of illuminating the optical marker.

7. The method of claim 6, wherein an illumination device provided on the module is used to illuminate the optical marker.

8. The method of claim 1, wherein:
    the module and the housing comprise first and second support portions respectively that are configured to support the module and the housing relative to one another when brought into engagement; and
    the step of placing the module and the housing relative to one another comprises engaging the first and second support portions.

9. The method of claim 8, wherein moving the module and the housing relative to one another comprises moving one of the support portions within a channel defined by the other support portion.

10. The method of claim 1, wherein determining the position of the optical marker in the field-of-view of the camera comprises:
comparing the camera output with the template;
determining a difference between the position of the optical marker in the field-of-view of the camera and the predetermined location of the optical marker in the field-of-view of the camera; and
determining an extent to which the camera and the optical marker should be moved relative to one another to offset the difference between the position of the optical marker and the predetermined location of the optical marker.

11. The method of claim 10, further comprising continually monitoring the difference until the difference has been offset.

12. The method of claim 1, wherein moving the module and the housing relative to one another based on the comparing comprises using one or more robotic arms.

13. A system for assembling an apparatus for determining an amount of dose delivered by an injection device, the system comprising:

a robotic arm for placing a module and a housing relative to one another, the housing being supported relative to an object having an optical marker, the object corresponding in a shape to a part of an injection device to which the supplemental device is configured to be coupled in use, the module comprising a camera for generating a camera output indicative of a scene in the field-of-view of the camera, and the robotic arm for moving the module and the housing relative to one another until the optical marker is at a predetermined location in the field-of-view of the camera;
a peripheral processing device for using the camera output to determine the position of the optical marker in the field-of-view of the camera and for comparing the position of the optical marker with a template indicative of the predetermined location of the optical marker in the field-of-view of the camera;
and
a fixation device for fixing a position of the module relative to the housing when the optical marker is at the predetermined location in the field-of-view of the camera.

14. The system of claim 13, wherein the fixation device comprises a clamping device, an adhering device, or a welding device.

* * * * *